(12) United States Patent
Meeks

(10) Patent No.: US 7,907,269 B2
(45) Date of Patent: Mar. 15, 2011

(54) SCATTERED LIGHT SEPARATION

(75) Inventor: Steven W. Meeks, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 12/822,253

(22) Filed: Jun. 24, 2010

(65) Prior Publication Data

US 2011/0019197 A1    Jan. 27, 2011

Related U.S. Application Data

(60) Provisional application No. 61/228,030, filed on Jul. 23, 2009.

(51) Int. Cl.
   *G01N 21/88*     (2006.01)
   *G01N 21/00*     (2006.01)

(52) U.S. Cl. .......... 356/237.1; 356/237.4; 356/601; 356/638; 250/372

(58) Field of Classification Search .... 356/237.1–237.5, 356/601–602, 609, 624, 634–636, 638, 640, 356/445–446; 250/237, 492.2
See application file for complete search history.

(56) References Cited

U.S. PATENT DOCUMENTS

| 4,749,840 | A | * | 6/1988 | Piwczyk | 219/121.68 |
| 5,131,023 | A | * | 7/1992 | Yasugaki et al. | 378/43 |
| 5,266,806 | A | * | 11/1993 | Barber | 250/341.4 |
| 5,331,456 | A | * | 7/1994 | Horikawa | 359/350 |
| 5,420,689 | A | * | 5/1995 | Siu | 356/394 |
| 6,088,092 | A | * | 7/2000 | Chen et al. | 356/237.2 |
| 6,384,910 | B2 | * | 5/2002 | Vaez-Iravani et al. | 356/237.2 |
| 6,522,717 | B1 | * | 2/2003 | Murakami et al. | 378/43 |
| 6,538,730 | B2 | * | 3/2003 | Vaez-Iravani et al. | 356/237.2 |
| 6,954,266 | B2 | * | 10/2005 | Tomie | 356/237.1 |
| 7,005,649 | B1 | * | 2/2006 | Tezuka et al. | 250/372 |
| 7,274,445 | B1 | | 9/2007 | Meeks | |
| 7,630,068 | B2 | * | 12/2009 | Tanaka et al. | 356/237.1 |

* cited by examiner

*Primary Examiner* — Sang Nguyen

(74) *Attorney, Agent, or Firm* — Luedeka, Neely & Graham, P.C.

(57) ABSTRACT

An apparatus for detecting top scattered light from a substrate. A source directs a light onto a position on the substrate. The light thereby reflects off in a specular beam, scatters off the top surface, and scatters off a bottom surface of the substrate. An objective receives the top and bottom scattered light. The objective has a first focal point focused on the position on the top surface of the substrate, and a second focal point focused on a pinhole field stop. The pinhole field stop passes the top scattered light that is focused on the pinhole field stop, and blocks the bottom scattered light. A sensor receives and quantifies the top scattered light.

20 Claims, 4 Drawing Sheets

SCATTERED LIGHT SEPARATION

FIELD

This application claims all rights and priority on copending U.S. provisional patent application Ser. No. 61/228,030 filed Jul. 23, 2009. This invention relates to the field of optical inspection technology. More particularly, this invention relates to the optical inspection of transparent substrates and epitaxial layers deposited upon transparent substrates.

INTRODUCTION

Transparent substrates, such as silicon carbide and sapphire, are frequently used in the fabrication of light emitting diodes. Such transparent substrates are often polished on only a single side of the substrate. In such substrates, the upper active surface is polished and the lower inactive surface remains unpolished. If a conventional scatterometer is used to inspect the substrate, then it is difficult to inspect the polished upper surface. The laser beam from the scatterometer penetrates the transparent substrate and strikes the bottom unpolished surface. The scatter signal from the unpolished bottom surface typically overwhelms the signal from the defects on the top surface. As a result, it is difficult to detect any defects that might be present on the top surface of the substrate.

What is needed, therefore, is a system that overcomes problems such as those described above, at least in part.

SUMMARY OF THE CLAIMS

The above and other needs are met by an apparatus for detecting top scattered light from a top surface of a substrate. A light source directs a beam of light onto a focal position on the top surface of the substrate, where the substrate is at least partially transmissive to the beam of light. The beam of light thereby, (a) specularly reflects off of the top surface of the substrate to produce a specular beam, (b) scatters up off of the focal position on the top surface of the substrate to produce the top scattered light, and (c) refracts into the substrate and scatters up off of a bottom surface of the substrate to produce bottom scattered light. An objective receives the top scattered light and an unblocked portion of the bottom scattered light. The objective has a first focal point focused on the focal position on the top surface of the substrate, and a second focal point focused on a pinhole field stop. The pinhole field stop receives the top scattered light and the unblocked portion of the bottom scattered light, and passes the top scattered light that is focused on the pinhole field stop, and blocks the unblocked portion of the bottom scattered light. A sensor disposed opposite the objective across the pinhole field stop receives and quantifies the top scattered light.

In this manner, the apparatus according to the various embodiments of the present invention separates the scattered light from the bottom surface of the substrate from the scattered light from the top surface of the substrate before the scattered light from the bottom surface of the substrate can attain the sensor. Thus, the signal from the sensor can be analyzed for defects on the top surface of the substrate, without being confounded or overpowered by the scattered light from the bottom surface of the substrate.

In various embodiments according to this aspect of the invention, the beam of light is a laser beam. In some embodiments the beam of light is directed obliquely onto the focal position on the top surface of the substrate. In other embodiments the beam of light is directed onto the focal position normal to the top surface of the substrate. In some embodiments the substrate is formed of at least one of silicon carbide and sapphire. In some embodiments the top surface of the substrate is relatively polished compared to the bottom surface of the substrate, and the bottom surface of the substrate is relatively rough compared to the top surface of the substrate. In some embodiments the objective is an ellipsoid of revolution having a mirror-polished interior surface. In other embodiments the objective is an aberration-corrected microscope objective. In still other embodiments the objective is a reflective microscope objective having a primary spherical mirror and secondary spherical mirror. In some embodiments a beam block disposed at least one of adjacent or interior to the objective for blocking at least a portion of the bottom scattered light. In some embodiments the objective has a field of view of about five hundred microns and a numerical aperture of about 0.52.

According to another aspect of the invention there is described a method for detecting top scattered light from a top surface of a substrate. A beam of light is directed onto a focal position on the top surface of the substrate, where the substrate is at least partially transmissive to the beam of light. The beam of light thereby (a) specularly reflects off of the top surface of the substrate to produce a specular beam, (b) scatters up off of the focal position on the top surface of the substrate to produce the top scattered light, and (c) refracts into the substrate and scatters up off of a bottom surface of the substrate to produce bottom scattered light. The top scattered light and an unblocked portion of the bottom scattered light are received with an objective. The objective has a first focal point focused on the focal position on the top surface of the substrate, and a second focal point focused on a pinhole field stop. The top scattered light and the unblocked portion of the bottom scattered light are received with the pinhole field stop, which passes the top scattered light that is focused on the pinhole field stop and blocks the unblocked portion of the bottom scattered light. A sensor disposed opposite the objective across the pinhole field stop receives and quantifies the top scattered light.

In various embodiments according to this aspect of the invention, the beam of light is a laser beam. In some embodiments the beam of light is directed obliquely onto the focal position on the top surface of the substrate. In other embodiments the beam of light is directed onto the focal position normal to the top surface of the substrate. In some embodiments the objective is an ellipsoid of revolution having a mirror-polished interior surface. In other embodiments the objective is an aberration-corrected microscope objective. In still other embodiments the objective is a reflective microscope objective having a primary spherical mirror and secondary spherical mirror. In some embodiments at least a portion of the bottom scattered light is blocked with a beam block disposed at least one of adjacent or interior the objective. In some embodiments an output of the sensor is analyzed to detect defects on the top surface of the substrate.

According to yet another embodiment of the present invention there is described an apparatus for detecting top scattered light from a top surface of a transparent substrate, where the top surface of the substrate is relatively polished compared to the bottom surface of the substrate, and the bottom surface of the substrate is relatively rough compared to the top surface of the substrate. A light source obliquely directs a laser beam onto a focal position on the top surface of the substrate. The laser beam thereby (a) specularly reflects off of the top surface of the substrate to produce a specular beam, (b) scatters up off of the focal position on the top surface of the substrate to produce the top scattered light, and (c) refracts into the substrate and scatters up off of a bottom surface of the substrate to produce bottom scattered light.

An objective receives the top scattered light and an unblocked portion of the bottom scattered light. The objective has a first focal point focused on the focal position on the top surface of the substrate, and a second focal point focused on a pinhole field stop. The objective is a reflective microscope objective having a primary spherical mirror and secondary spherical mirror, with a field of view of about five hundred microns and a numerical aperture of about 0.52. A beam block is disposed at least one of adjacent or interior to the objective, and blocks at least a portion of the bottom scattered light. The pinhole field stop receives the top scattered light and the unblocked portion of the bottom scattered light, and passes the top scattered light that is focused on the pinhole field stop and blocks the unblocked portion of the bottom scattered light. A sensor is disposed opposite the objective across the pinhole field stop, and receives and quantifies the top scattered light.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
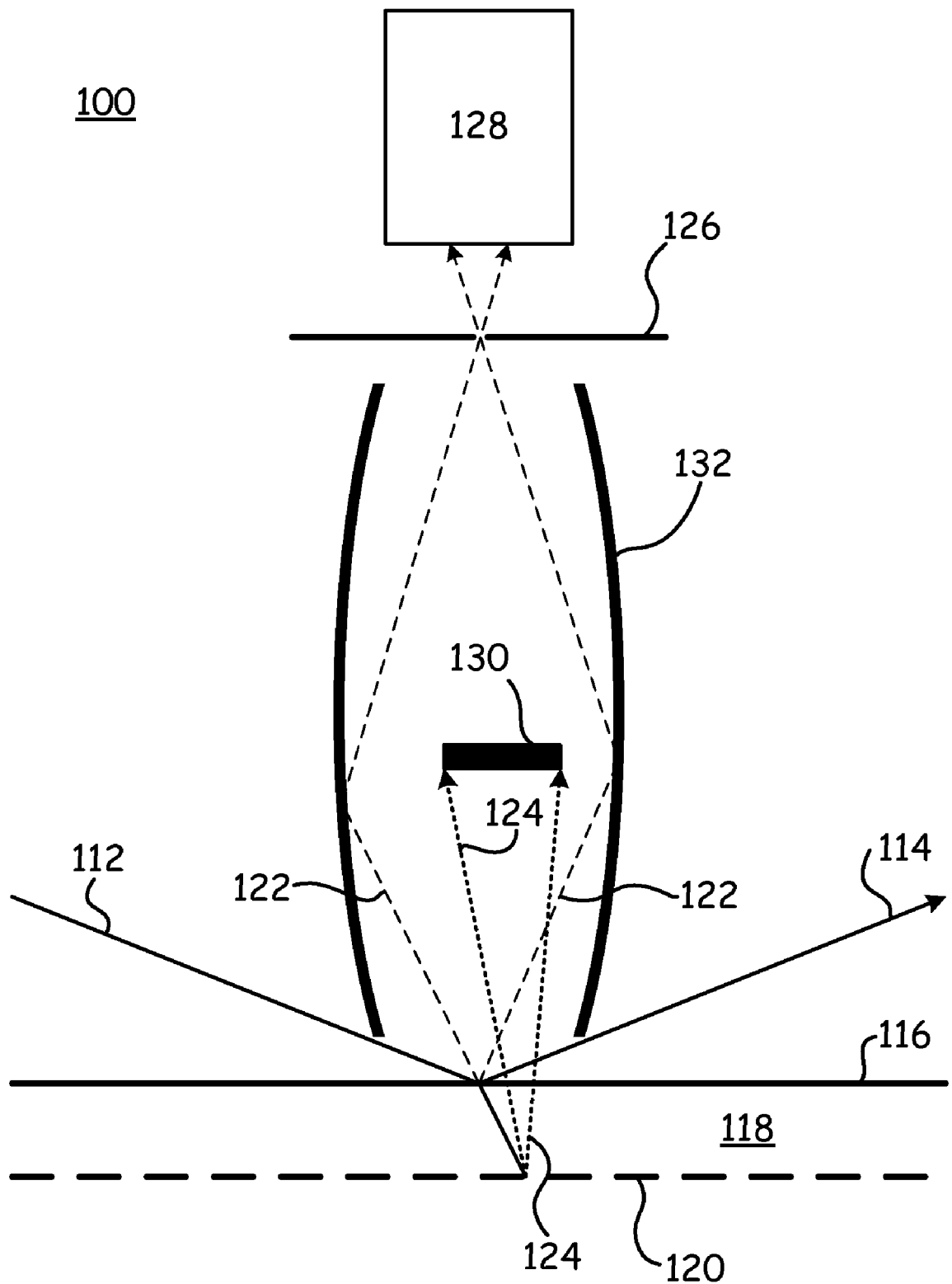
FIG. 1 depicts a collector objective for a scatterometer according to a first embodiment of the present invention.

With reference now to FIG. 1, there is depicted an embodiment 100 of the present invention, having an ellipsoidal collector 132 with an internal beam block 130 and field stop (pinhole) 126, used as a scattered light collector. The ellipsoidal collector 132, internal beam block 130, and field stop 126 provide a degree of isolation between the light 122 that is scattered off of the top surface 116 of the substrate 118, and the light 124 that is scattered off of the bottom surface 120 of the substrate 118.

An input laser beam 112 is directed beneath an internally-reflective ellipsoid of revolution 132. A portion of the input laser beam 112 specularly reflects off of the top surface 116 of the substrate 118 as a reflected beam 114, and a portion 122 of the input laser beam 112 is scattered from the top surface 116 into the ellipsoid 132. A portion of the input laser beam 112 refracts into the transparent substrate 118 and is scattered off of the unpolished bottom surface 120 of the substrate 118 as scattered light 124. The substrate 118 is formed of a material such as silicon carbide or sapphire.

Ellipsoid 132 is located with its first or lower foci at the top surface 116 of the transparent substrate 118, at the point where the input laser beam 112 reflects from the upper surface 116 of the substrate 118. The pinhole or field stop 126 is located at the second or upper foci of the ellipsoid 132. The portion of the scattered light 124 from the back surface 120 that does not reflect from the mirrored internal surfaces of the ellipsoid of revolution 132 is blocked by an absorbing beam block 130, placed internally to the ellipsoid 132. The scattered light 122 that originates from the lower foci is thus directed to the second foci and passes through the pinhole 126, and is received by a photomultiplier tube 128, or some other light sensor.

Figure 2:
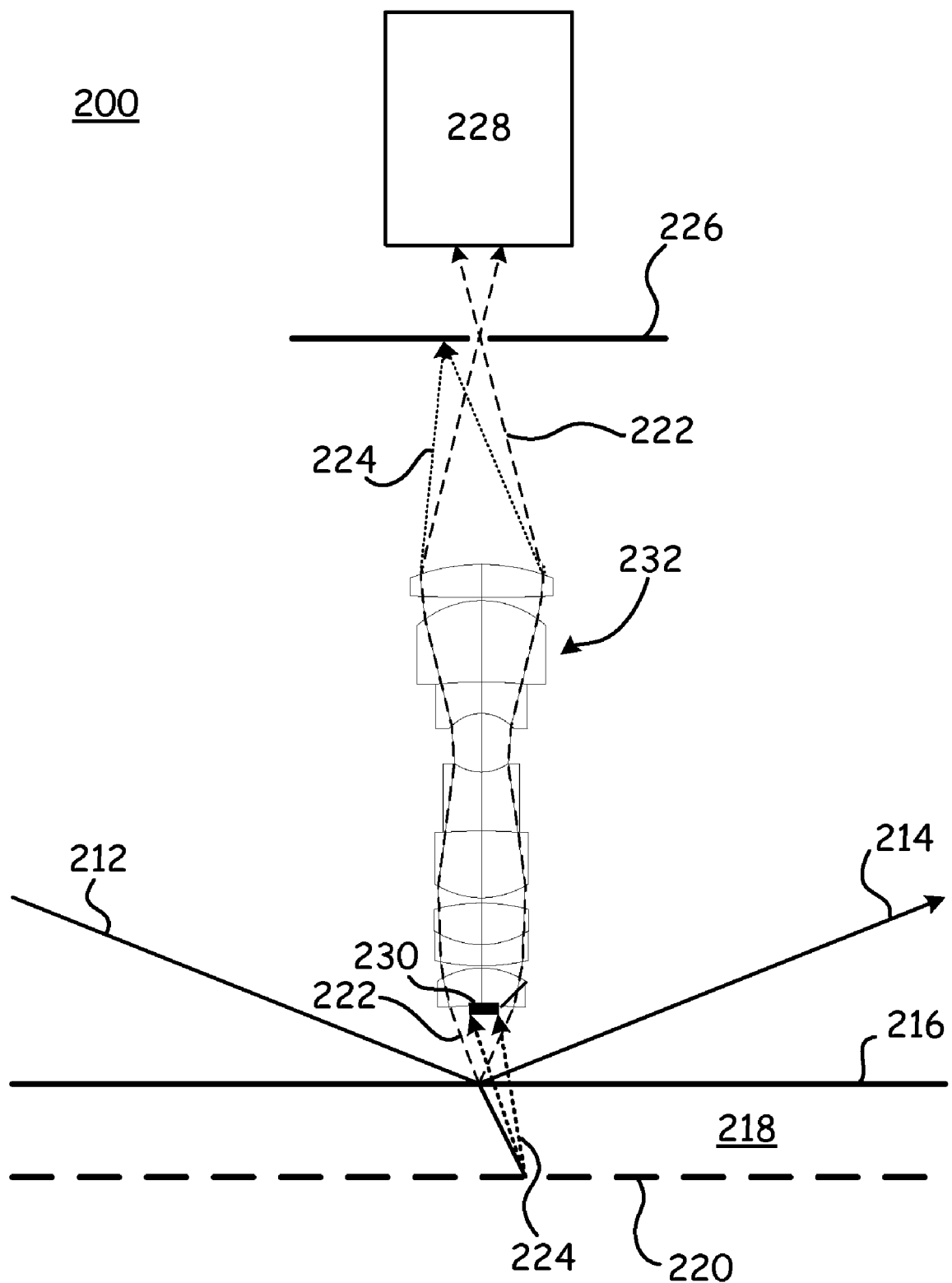
FIG. 2 depicts a collector objective for a scatterometer according to a second embodiment of the present invention.

With reference to FIG. 2, there is depicted a second embodiment 200 of an aberration-corrected microscope objective 232 that is used to collect the scattered light 222 from the top surface 216. Laser light 212 is brought in beneath the objective 232. A portion 214 specularly reflects from the top surface 216, and a portion 222 scatters from the top surface 216. Another portion of the beam 212 refracts into the transparent substrate 218 and scatters from the bottom unpolished surface 220 as scattered light 224. The scattered light 224 from the bottom surface 220 is partially blocked by an absorbing beam block 230 placed beneath the objective 232. The objective 232 is focused at the top surface 216 at the point where the laser beam 212 reflects off the surface 216 of the substrate 218.

When the scattered light 224 from the bottom surface 220 appears at the upper conjugate of the objective 232, it is shifted to the left (in the embodiment as depicted). A pinhole 226 placed at the upper conjugate separates the top scattered light 222 and the bottom scattered light 224. The scattered light 222 from the top surface 216 passes through the pinhole 226 and is detected by the sensor 228.

Because the microscope objective 232 is an imaging device with a relatively wider field of view than the ellipsoid 132, the scattered light 224 from the bottom surface 220 simply appears as an out of focus spot with a central hole (due to the presence of beam absorber 230). In this manner, the microscope objective 232 is quite successful in separating the light 222 scattered from the top surface 216 and the light 224 scattered from the bottom surface 220.

The operation of the beam block 230 is further clarified in an embodiment where a normally incident beam (not depicted) is directed onto and scatters from the top surface 216 and the bottom surface 220. The scattered light 222 from the top surface 216 follows the path through the pinhole 226. The scattered light 224 from the bottom surface 220 follows the same path, except that it appears as an out of focus spot with a central hole surrounding the focused beam 222 at the location of the pinhole 226. The central hole is created by the absorbing beam block 230. The pinhole 226 only passes the scattered light 222 from the top surface 216. It is the presence of the beam block 230, combined with the imaging nature of the microscope objective 232, that allows this separation of the light 224 scattered from the bottom surface 220 and the light 222 scattered from the top surface 216.

Figure 3:
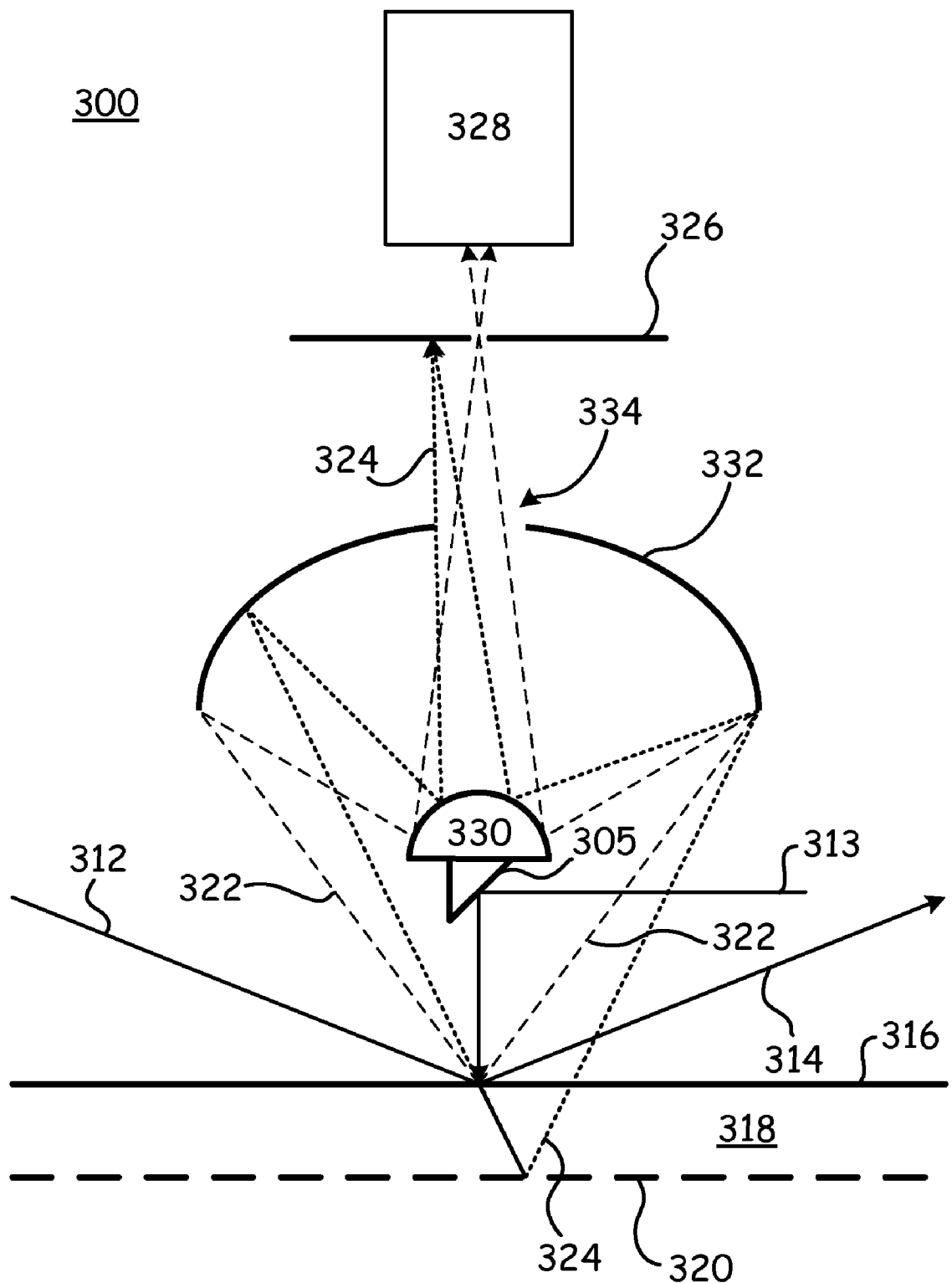
FIG. 3 depicts a collector objective for a scatterometer according to a third embodiment of the present invention.

With reference now to FIG. 3, there is depicted an embodiment 300 of the present invention. A laser beam 312 is directed onto the top surface 316 of the substrate 318, and specularly reflects off of the top surface 316 of the substrate 318 as reflected beam 314. Some of the laser beam 312 scatters from the polished top surface 316 of the substrate 318 as scattered light 322, and some of the laser beam 312 refracts into the substrate 318 and scatters from the unpolished bottom surface 320 as scattered light 324.

The scattered lights 322 and 324 are received by a reflective microscope objective composed of a primary spherical mirror 332, and are reflected onto a secondary spherical mirror 330, before passing through the port 334 in the primary mirror 332. Secondary spherical mirror 330 is designed to obstruct less than about twenty percent of the total light scattered from the surface so as to optimize the sensitivity of the system 300. In one embodiment, the objective 332 has a five hundred micron field of view with a 0.52 numerical aperture and a long working distance. The focal point of the objective 332 is located at the upper surface 316 at a point where the laser beam 312 reflects off of the upper surface 316.

Once the light 322 and the light 324 are outside of the port 334, the scattered light 322 from the top surface 316 passes through the pinhole field stop 326 to attain the light sensor 328, while the scattered light 324 from the unpolished backside 320 of the substrate 318 comes at a different angle and is blocked by the pinhole field stop 326 from attaining the light sensor 328.

It is sometimes desirable to bring in laser light at different angles of incidence to the substrate 318. System 300 also depicts a normally-incident beam 313 that reflects off of a forty-five degree turning mirror 305 before striking the surface 316. In this embodiment, the scattered light 324 from the bottom surface 320 is not directed to the left or right of the pinhole 326, but appears as a bright spot with a hole in its center caused by the secondary mirror 330. The hole is centered on the pinhole 326, which separates the scattered light 322 from the top surface 316 from the scattered light 324 from the bottom surface 320 of the transparent substrate 318 in that embodiment.

It is appreciated that embodiment 300 is optimized for separating the scattered light 322 from the top surface 316 from the scattered light 324 from the bottom surface 320 of the transparent substrate 318. This embodiment 300 uses an all-reflective optical design, where no bulk scatter is generated and only two surfaces (the primary mirror 332 and the secondary mirror 330) contribute to the residual scatter due to surface roughness.

Figure 4:
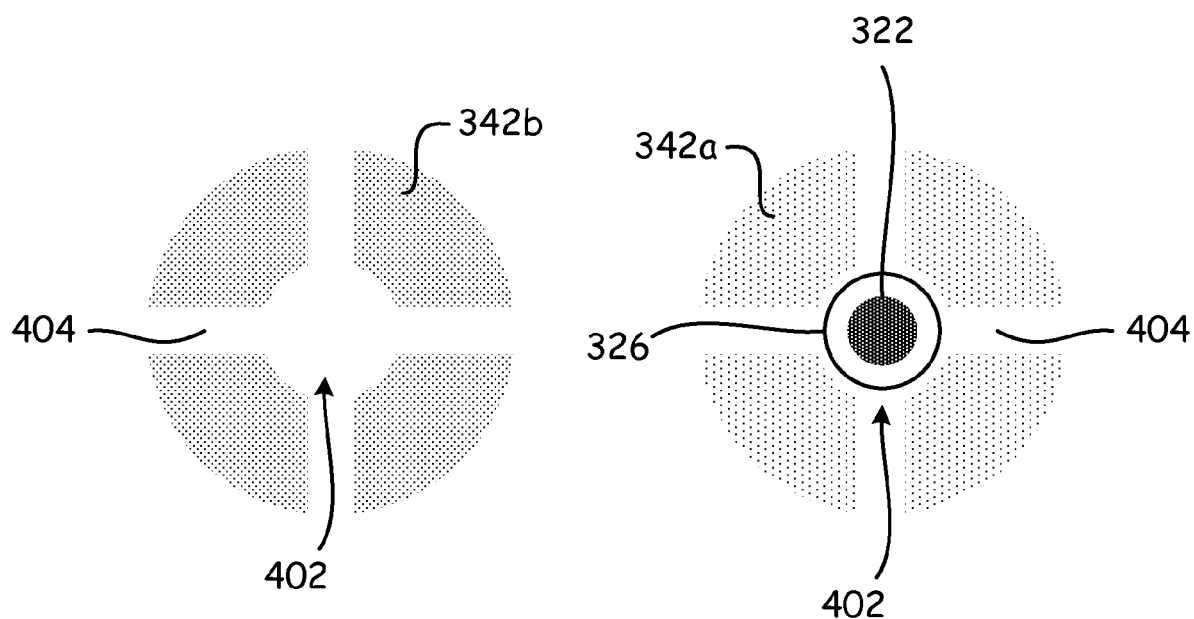
FIG. 4 depicts a light pattern from a collector objective for a scatterometer according to the third embodiment of the present invention.

By way of further explanation, FIG. 4 depicts the scattered light patterns that appear on the plane of the pinhole 326. The focused scattered light 322 from the top surface 316 of the substrate 318 appears at the center of the pinhole 326, surrounded by the defocused scattered light 324a from the bottom surface 320 of the substrate 318 from the normally incident beam 313.

The hole 402 in the scattered light 324a is created by the secondary mirror 330. The cross members 404 in the scattered light 324a (depicted by way of example) are caused by the support structures (not depicted in FIG. 3) that hold the secondary mirror 330 in place. The scattered light pattern 324b to the left of the pinhole 326 is created by the scattered light 324 from the bottom surface 320 that originates from the oblique beam 312. In this embodiment, the pattern 342b is a defocused spot with a hole 402 surrounded by cross members 404.

In some instances it is desired to use different wavelengths for the normal beam 313 and the oblique beam 312. In such an embodiment, the reflective objective 332 is particularly advantageous because it exhibits no chromatic aberration.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for detecting top scattered light from a top surface of a substrate, the apparatus comprising:
    a light source for directing a beam of light onto a focal position on the top surface of the substrate, where the substrate is at least partially transmissive to the beam of light, the beam of light thereby,
        (a) specularly reflecting off of the top surface of the substrate to produce a specular beam,
        (b) scattering up off of the focal position on the top surface of the substrate to produce the top scattered light, and
        (c) refracting into the substrate and scattering up off of a bottom surface of the substrate to produce bottom scattered light,
    an objective for receiving the top scattered light and an unblocked portion of the bottom scattered light, the objective having a first focal point focused on the focal position on the top surface of the substrate, and a second focal point focused on a pinhole field stop,
    the pinhole field stop for receiving the top scattered light and the unblocked portion of the bottom scattered light, and passing the top scattered light that is focused on the pinhole field stop and blocking the unblocked portion of the bottom scattered light, and
    a sensor disposed opposite the objective across the pinhole field stop for receiving and quantifying the top scattered light.

2. The apparatus of claim 1, wherein the beam of light is a laser beam.

3. The apparatus of claim 1, wherein the beam of light is directed obliquely onto the focal position on the top surface of the substrate.

4. The apparatus of claim 1, wherein the beam of light is directed onto the focal position normal to the top surface of the substrate.

5. The apparatus of claim 1, wherein the substrate is formed of at least one of silicon carbide and sapphire.

6. The apparatus of claim 1, wherein the top surface of the substrate is relatively polished compared to the bottom surface of the substrate, and the bottom surface of the substrate is relatively rough compared to the top surface of the substrate.

7. The apparatus of claim 1, wherein the objective is an ellipsoid of revolution having a mirror-polished interior surface.

8. The apparatus of claim 1, wherein the objective is an aberration-corrected microscope objective.

9. The apparatus of claim 1, wherein the objective is a reflective microscope objective having a primary mirror and secondary mirror.

10. The apparatus of claim 1, further comprising a beam block disposed at least one of adjacent or interior to the objective for blocking at least a portion of the bottom scattered light.

11. The apparatus of claim 1, wherein the objective has a field of view of about five hundred microns and a numerical aperture of about 0.52.

12. A method for detecting top scattered light from a top surface of a substrate, the method comprising the steps of:
    directing a beam of light onto a focal position on the top surface of the substrate, where the substrate is at least partially transmissive to the beam of light, the beam of light thereby,
        (a) specularly reflecting off of the top surface of the substrate to produce a specular beam, (b) scattering up off of the focal position on the top surface of the substrate to produce the top scattered light, and (c) refracting into the substrate and scattering up off of a bottom surface of the substrate to produce bottom scattered light, receiving the top scattered light and an unblocked portion of the bottom scattered light with an objective, the objective having a first focal point focused on the focal position on the top surface of the substrate, and a second focal point focused on a pinhole field stop, receiving the top scattered light and the unblocked portion of the bottom scattered light with the pinhole field stop, and passing the top scattered light that is focused on the pinhole field stop and blocking the unblocked portion of the bottom scattered light, and receiving and quantifying the top scattered light with a sensor disposed opposite the objective across the pinhole field stop.

13. The method of claim 12, wherein the beam of light is a laser beam.

14. The method of claim 12, wherein the beam of light is directed obliquely onto the focal position on the top surface of the substrate.

15. The method of claim 12, wherein the beam of light is directed onto the focal position normal to the top surface of the substrate.

16. The method of claim 12, wherein the objective is an ellipsoid of revolution having a mirror-polished interior surface.

17. The method of claim 12, wherein the objective is an aberration-corrected microscope objective.

18. The method of claim 12, wherein the objective is a reflective microscope objective having a primary mirror and secondary mirror.

19. The method of claim 12, further comprising analyzing an output of the sensor to detect defects on the top surface of the substrate.

20. An apparatus for detecting top scattered light from a top surface of a transparent substrate, where the top surface of the substrate is relatively polished compared to the bottom surface of the substrate, and the bottom surface of the substrate is relatively rough compared to the top surface of the substrate, the apparatus comprising:

a light source for obliquely and normally directing a laser beam onto a focal position on the top surface of the substrate, the laser beam thereby, (a) specularly reflecting off of the top surface of the substrate to produce a specular beam, (b) scattering up off of the focal position on the top surface of the substrate to produce the top scattered light, and (c) refracting into the substrate and scattering up off of a bottom surface of the substrate to produce bottom scattered light, an objective for receiving the top scattered light and an unblocked portion of the bottom scattered light, the objective having a first focal point focused on the focal position on the top surface of the substrate, and a second focal point focused on a pinhole field stop, wherein the objective is a reflective microscope objective having a primary spherical mirror and secondary spherical mirror, the objective having a field of view of about five hundred microns and a numerical aperture of about 0.52, a beam block disposed at least one of adjacent or interior to the objective for blocking at least a portion of the bottom scattered light, the pinhole field stop for receiving the top scattered light and the unblocked portion of the bottom scattered light, and passing the top scattered light that is focused on the pinhole field stop and blocking the unblocked portion of the bottom scattered light, and a sensor disposed opposite the objective across the pinhole field stop for receiving and quantifying the top scattered light.

* * * * *